US011135973B2

(12) United States Patent
Pinckney (10) Patent No.: US 11,135,973 B2
(45) Date of Patent: Oct. 5, 2021

(54) DRIVER ALERT SYSTEM TO PREVENT ABANDONMENT OF A PERSON OR AN ANIMAL IN A VEHICLE AND COMPONENTS THEREOF

(71) Applicant: Akaisha Pinckney, Goose Creek, SC (US)

(72) Inventor: Akaisha Pinckney, Goose Creek, SC (US)

(*) Notice: Subject to any disclaimer, the term of this patent is extended or adjusted under 35 U.S.C. 154(b) by 0 days.

(21) Appl. No.: 16/382,415

(22) Filed: Apr. 12, 2019

(65) Prior Publication Data

US 2020/0324698 A1  Oct. 15, 2020

(51) Int. Cl.
| B60Q 9/00 | (2006.01) |
| G08B 21/02 | (2006.01) |
| A61B 5/1455 | (2006.01) |
| A61B 5/0205 | (2006.01) |
| A61B 5/11 | (2006.01) |
| A61B 5/00 | (2006.01) |
| A61B 5/08 | (2006.01) |
| A61B 5/024 | (2006.01) |

(52) U.S. Cl.
CPC ............ *B60Q 9/00* (2013.01); *A61B 5/02055* (2013.01); *A61B 5/1113* (2013.01); *A61B 5/14552* (2013.01); *A61B 5/746* (2013.01); *G08B 21/02* (2013.01); *A61B 5/024* (2013.01); *A61B 5/0816* (2013.01)

(58) Field of Classification Search
CPC ..... B60Q 9/00; A61B 5/02055; A61B 5/1113; A61B 5/14552; A61B 5/746; A61B 5/024; A61B 5/0816; G08B 21/02
See application file for complete search history.

(56) References Cited

U.S. PATENT DOCUMENTS

| 6,289,747 B1 * | 9/2001 | Billen ................... H01C 10/12 73/862.046 |
| 6,489,893 B1 * | 12/2002 | Richards ................. G01S 13/42 340/573.1 |
| 6,992,588 B1 * | 1/2006 | Santosstefano ........... B62B 9/00 119/770 |
| 6,998,988 B1 * | 2/2006 | Kalce .................... B60N 2/002 340/457.1 |
| 7,230,530 B1 * | 6/2007 | Almquist ............... B60N 2/002 180/271 |

(Continued)

OTHER PUBLICATIONS

Martin Woolley, Bluetooth Technology Protecting Your Privacy, Apr. 2, 2015, SIG Bluetooth.com, pp. 1-3 (Year: 2015).*

*Primary Examiner* — Joseph H Field
*Assistant Examiner* — Rufus C Point
(74) *Attorney, Agent, or Firm* — The Iwashko Law Firm, PLLC; Lev Ivan Gabriel Iwashko (57) ABSTRACT

An alert system to prevent abandonment of a living being in a vehicle, the alert system including a pad removably disposed on at least a portion of an interior of the vehicle to monitor and store data related to the living being in response to the living being being disposed on the pad, and at least one master fob to receive the data related to the living being from the pad and to generate an alert in response to the master fob being moved a predetermined distance away from the pad and based on at least a portion of the received data indicating that that the living being is disposed on the pad.

15 Claims, 2 Drawing Sheets

(56) References Cited

U.S. PATENT DOCUMENTS

| | | | | |
|---|---|---|---|---|
| 7,908,777 | B1* | 3/2011 | Beardsley | B60N 2/28 40/320 |
| 8,618,926 | B1* | 12/2013 | Thompson | G08G 1/205 340/522 |
| 9,569,948 | B1* | 2/2017 | Platt | G08B 21/22 |
| 2003/0130822 | A1* | 7/2003 | Steele | A63F 13/355 702/188 |
| 2004/0246136 | A1* | 12/2004 | Sanoner | G08B 21/02 340/573.1 |
| 2007/0057799 | A1* | 3/2007 | Monzo | B60N 2/002 340/573.1 |
| 2007/0075574 | A1* | 4/2007 | James | B60N 2/28 297/217.3 |
| 2007/0268119 | A1* | 11/2007 | Cram | B60Q 9/00 340/457 |
| 2008/0100431 | A1* | 5/2008 | Monzo | B60Q 9/00 340/457 |
| 2008/0157942 | A1* | 7/2008 | Payne | B60R 25/1004 340/426.12 |
| 2008/0316043 | A1* | 12/2008 | Gomes | B60N 2/28 340/686.6 |
| 2009/0212955 | A1* | 8/2009 | Schoenberg | G08B 21/24 340/573.1 |
| 2010/0046553 | A1* | 2/2010 | Daigle | H04L 69/22 370/474 |
| 2011/0053664 | A1* | 3/2011 | Shim | H04M 1/724 455/575.3 |
| 2012/0232749 | A1* | 9/2012 | Schoenberg | B60N 2/28 701/36 |
| 2013/0109342 | A1* | 5/2013 | Welch | G08B 21/22 455/404.2 |
| 2014/0015664 | A1* | 1/2014 | Watson | G08B 21/24 340/457.1 |
| 2014/0253314 | A1* | 9/2014 | Rambadt | B60N 2/002 340/457.1 |
| 2015/0228172 | A1* | 8/2015 | Dezur-Ahola | B60N 2/28 340/522 |
| 2016/0089084 | A1* | 3/2016 | Sugiyama | A61B 5/25 600/372 |
| 2016/0210843 | A1* | 7/2016 | Killette | B60N 2/26 |
| 2016/0296157 | A1* | 10/2016 | Girouard | G16H 40/67 |
| 2018/0126950 | A1* | 5/2018 | Aiderman | B60R 25/24 |
| 2018/0354443 | A1* | 12/2018 | Ebrahimi | B60N 2/2812 |
| 2018/0361887 | A1* | 12/2018 | Labelle | G08B 21/22 |
| 2019/0125224 | A1* | 5/2019 | Kamath | G16H 40/63 |
| 2019/0355230 | A1* | 11/2019 | Miller | G08B 21/22 |
| 2019/0374841 | A1* | 12/2019 | Baillie | A63B 71/0622 |

* cited by examiner

DRIVER ALERT SYSTEM TO PREVENT ABANDONMENT OF A PERSON OR AN ANIMAL IN A VEHICLE AND COMPONENTS THEREOF

BACKGROUND

1. Field

The present general inventive concept relates generally to an alert system, and particularly, to an alert system to prevent abandonment of a person or an animal in a vehicle, and components thereof.

2. Description of the Related Art

Many consumers have hectic and demanding schedules, which often cause lapses in judgment resulting in drivers sometimes leaving children, elderly, and/or pets in vehicles unattended. Leaving a child, an elder, and/or a pet in a vehicle can potentially lead to a fatal incident, such as overheating and/or dehydration.

Presently, there are limited products available on the market capable of immediately alerting drivers of such an event in a matter that could assist the child, the elder, and/or the pet, before it is too late.

Therefore, there is a need for an alert system to prevent abandonment of a person and/or an animal in a vehicle.

SUMMARY

The present general inventive concept provides an alert system to prevent abandonment of a person or an animal in a vehicle, and components thereof.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing an alert system to prevent abandonment of a living being in a vehicle, the alert system including a pad removably disposed on at least a portion of an interior of the vehicle to monitor and store data related to the living being in response to the living being being disposed on the pad, and at least one master fob to receive the data related to the living being from the pad and to generate an alert in response to the master fob being moved a predetermined distance away from the pad and based on at least a portion of the received data indicating that that the living being is disposed on the pad.

The alert system may further include a pulse oximeter to detect a level of oxygen saturation in blood of the living being.

The pulse oximeter may monitor the level of oxygen saturation in the blood of the living being in response to the living being disposed on the pad.

The pulse oximeter may monitor the level of oxygen saturation in the blood of the living being in response to the pulse oximeter being connected to the living being.

The pulse oximeter may be disposed within at least a portion of the pad.

The pulse oximeter may be a wearable device.

The alert system may further include a small fob removably connected to the living being to receive the data related to the living being from the pad.

The small fob may transmit the data related to the living being to the at least one master fob.

The alert system may further include a computing device including an app executed thereon, the app monitoring the data related to the living being received from the pad.

The app may alert a third party in response to at least one of the user's failure to return to the vehicle within a predetermined amount of time and the user's failure to assist the living being.

Assisting the living being may be removing the living being from the vehicle.

The app may randomly generate a code to be stored on the pad and another at least one master fob, such that the another at least one master fob may receive the data related to the living being from the pad.

The data related to the living being is at least one of a weight of the living being, a temperature level of the living being, a movement of the living being, a heartbeat of the living being, and breathing of the living being.

A pad to monitor data related to the living being in a vehicle, the pad including at least one sensor disposed within at least a portion of the pad to detect information relating to the living being, and a communication unit to send the information related to the living being to an external device such that the external device is alerted that the living being is disposed on the pad.

The pad may further include a pulse oximeter disposed within at least a portion of the pad to monitor a level of oxygen saturation in blood of the living being.

The information relating to the living being may be at least one of a weight of the living being and a temperature level of the living being.

A master fob, including a body, an indentation disposed on at least a portion of an end of the body to store an alert unit therein, a communication unit disposed within at least a portion of the body to receive data related to a living being from an external device, a processing unit disposed within at least a portion of the body to generate an alert in response to the body being moved a predetermined distance away from a vehicle and based on at least a portion of the received data indicating that that the living being is disposed in the vehicle, and an alert unit disposed within at least a portion of the indentation to generate at least one of an illumination, a sound, and a vibration in response to the alert and the at least a portion of the received data indicating that that the living being is disposed in the vehicle.

The alert unit is at least one of a light, a beeper, and a haptic unit.

The master fob may further include a button disposed on at least a portion of the body to terminate the alert signal.

BRIEF DESCRIPTION OF THE DRAWINGS

These and/or other features and utilities of the present generally inventive concept will become apparent and more readily appreciated from the following description of the embodiments, taken in conjunction with the accompanying drawings of which.

DETAILED DESCRIPTION

Various example embodiments (a.k.a., exemplary embodiments) will now be described more fully with reference to the accompanying drawings in which some example embodiments are illustrated. In the figures, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like/similar elements throughout the detailed description.

It is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

LIST OF COMPONENTS

Alert System 100
Pad 110
Top Surface 110a
Bottom Surface 110b
Sensor 111
Pulse Oximeter 112
Control Unit 113
Processing Unit 113a
Communication Unit 113b
Storage Unit 113c
Power Source 114
Small Fob 120
Body 121
Control Unit 122
Processing Unit 122a
Communication Unit 122b
Power Source 123
Master Fob 130
Body 131
Indentation 131a
Light 132
Beeper 133
Button 134
Control Unit 135
Processing Unit 135a
Communication Unit 135b
Storage Unit 135c
Haptic Unit 136
Power Source 137
Computing Device 140
Input Unit 141
Display Unit 142
Processing Unit 143
Communication Unit 144
Storage Unit 145

Figure 1:
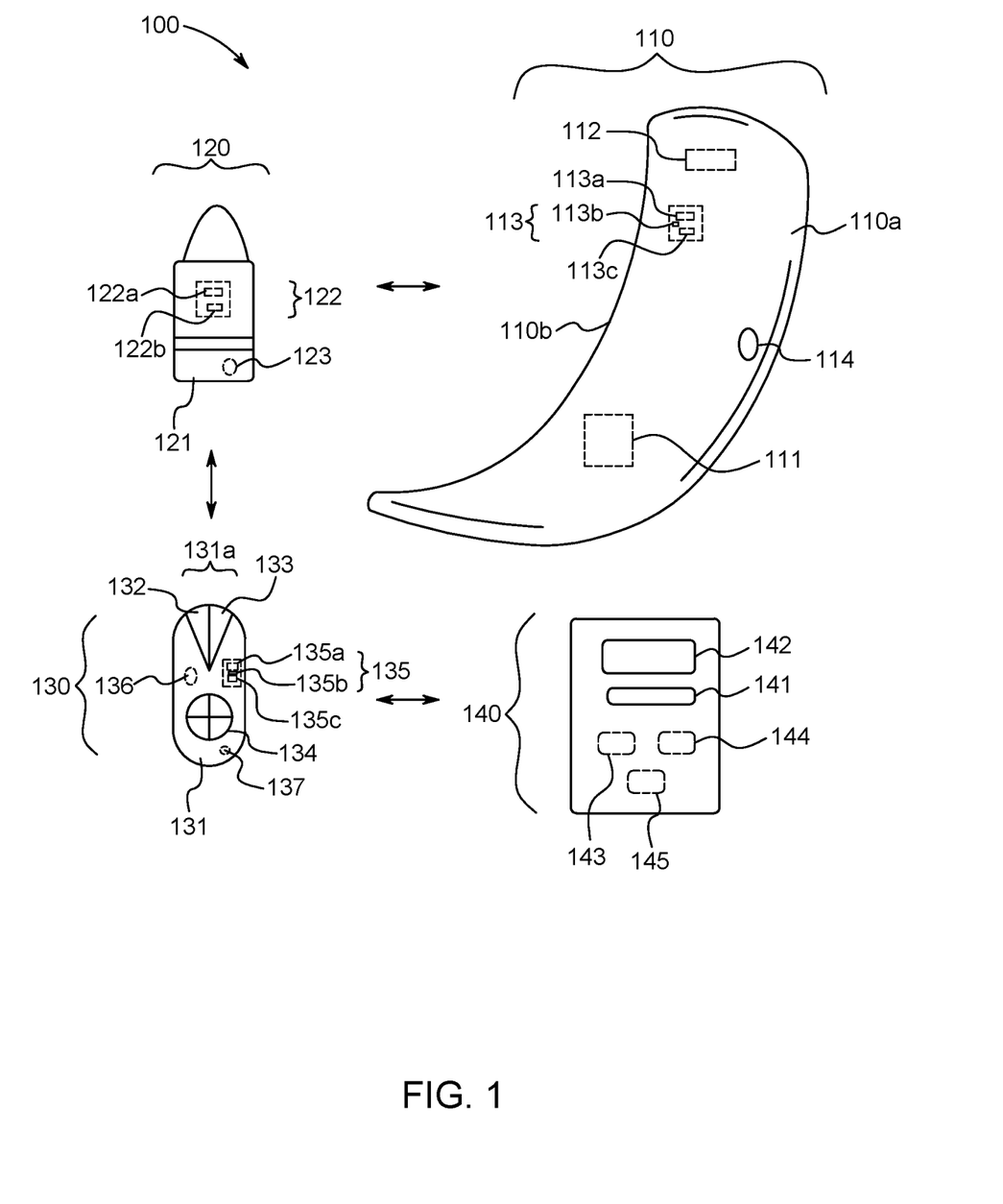
FIG. 1 illustrates a front perspective view of an alert system, according to an exemplary embodiment of the present general inventive concept.

FIG. 1 illustrates a front perspective view of an alert system 100, according to an exemplary embodiment of the present general inventive concept.

Figure 2:
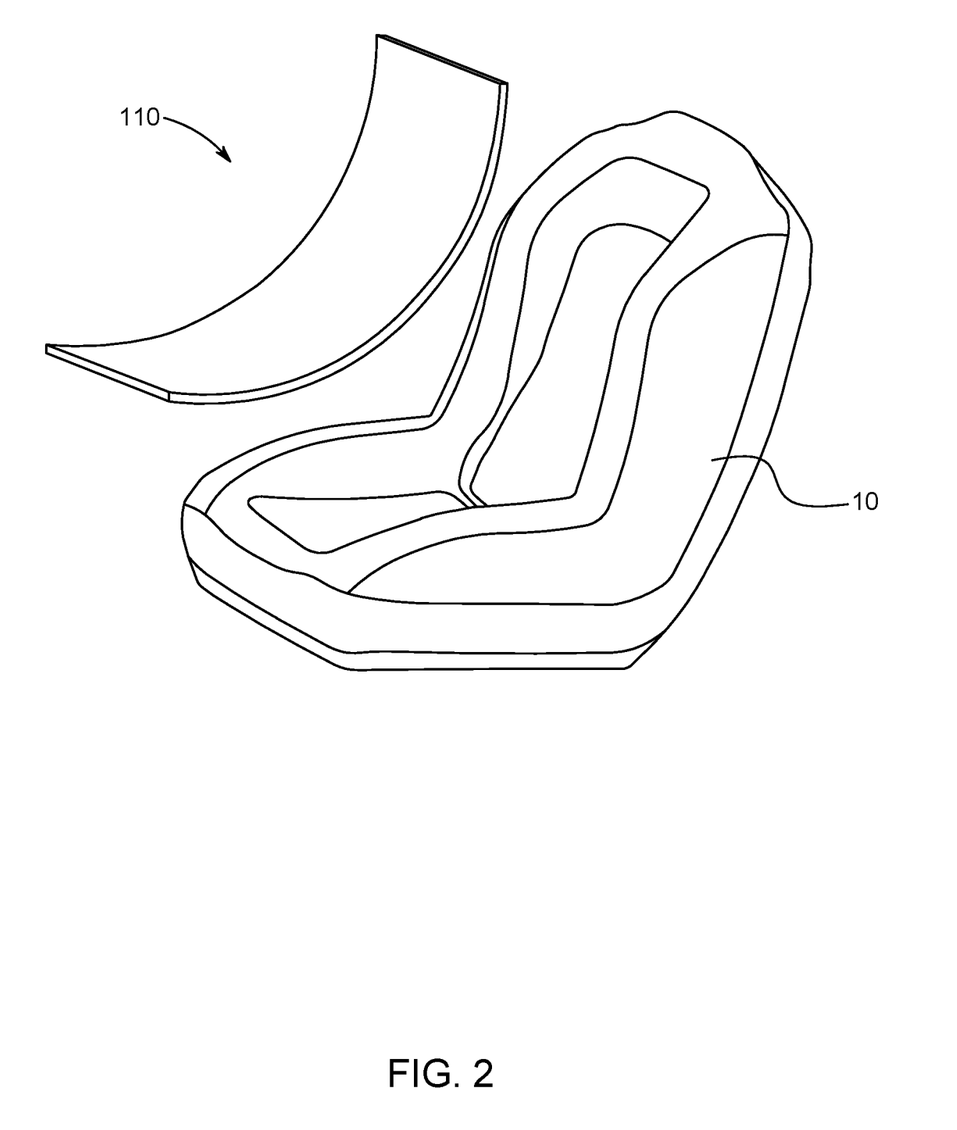
FIG. 2 illustrates an exploded view of a pad disposed on a vehicle seat, according to an exemplary embodiment of the present general inventive concept.

FIG. 2 illustrates an exploded view of a pad 110 disposed on a vehicle seat 10, according to an exemplary embodiment of the present general inventive concept.

The alert system 100 may be constructed from at least one of metal, plastic, glass, and rubber, etc., but is not limited thereto.

The alert system 100 may include the pad 110, a small fob 120, at least one master fob 130, and a computing device 140, but is not limited thereto.

Referring to FIG. 1, the pad 110 is illustrated to have an arcuate shape. However, the pad 110 may be flat and may be a square prism, a rectangular prism, a circular prism, a hexagonal prism, an octagonal prism, or any other shape known to one of ordinary skill in the art, but is not limited thereto.

Furthermore, the pad 110 may be flexible to assume the shape of any surface upon which it is placed.

The pad 110 may include a top surface 110a, a bottom surface 110b, at least one sensor 111, a pulse oximeter 112, a control unit 113, and a power source 114, but is not limited thereto.

The pad 110 may be placed on a top surface of a child seat, the vehicle seat 10, and/or within an animal container in a vehicle. Specifically, the bottom surface 110b may be placed against the top surface of the child seat, the vehicle seat, and/or within the animal container, such that a child, a person, and/or an animal may sit on the top surface 110a of the pad 110. For ease of description, the child, the person, and/or the animal will be hereinafter referred to as a living being. Alternatively, the pad 110 may be inversely installed, such that the living being may sit on the bottom surface 110b without any difference in functionality.

The at least one sensor 111 may include at least one of a weight sensor, a temperature sensor, a movement sensor, a heartbeat sensor, and a breathing sensor, but is not limited thereto.

The at least one sensor 111 may be disposed within at least a portion of the pad 110. The at least one sensor 111 may activate in response to the living being disposed on the pad 110. Specifically, the at least one sensor 111 may detect a weight of the living being in response to the living being disposed on the pad 110. Also, the at least one sensor 111 may monitor a temperature level of the living being, a movement of the living being, a heartbeat of the living being, and/or breathing of the living being.

The pulse oximeter 112 may be disposed within at least a portion of the pad 110. Alternatively, the pulse oximeter 112 may be a wearable device that is separate from the pad 110. As such, the pulse oximeter 112 may be a bracelet, an anklet, an attachment on a finger, an attachment on a foot, an attachment on an earlobe, a strap, a watch, and an armband, etc., but is not limited thereto.

Moreover, the pulse oximeter 112 may activate in response to the living being disposed on the pad 110. Alternatively, the pulse oximeter 112 may activate in response to the pulse oximeter 112 being connected to the living being. The pulse oximeter 112 may monitor a level of oxygen saturation in blood of the living being.

The pulse oximeter 112 may measure the level of oxygen saturation in the blood of the living being to indicate that the living being may be present in the vehicle. In other words, the pulse oximeter 112 may detect fluctuations in the level of oxygen saturation as a result of the living being breathing in the vehicle while the vehicle is turned off. As such, air within the vehicle may no longer circulate and cause the level of oxygen saturation in the blood of the living being to decrease.

As such, the pad 110 may monitor data related to the living being, such as presence based on the weight of the living being, the temperature level of the living being, the movement of the living being, the heartbeat of the living being, the breathing of the living being, and/or the level of oxygen saturation in the blood of the living being. Furthermore, the data related to the living being may be generated only in response to the living being connecting to the pad 110 and/or the pulse oximeter 112.

The control unit 113 may include a processing unit 113a, a communication unit 113b, and a storage unit 113c, but is not limited thereto.

The control unit 113 may be disposed within at least a portion of the pad 110.

The processing unit 113a (or central processing unit, CPU) may include electronic circuitry to carry out instructions of a computer program by performing basic arithmetic, logical, control and input/output (I/O) operations specified by the instructions. The processing unit 113a may include an arithmetic logic unit (ALU) that performs arithmetic and logic operations, processor registers that supply operands to the ALU and store the results of ALU operations, and a control unit that fetches instructions from memory and "executes" them by directing the coordinated operations of the ALU, registers and other components. The processing unit 113a may also include a microprocessor and a microcontroller.

The communication unit 113b may include a device capable of wireless or wired communication between other wireless or wired devices via at least one of Wi-Fi, Wi-Fi Direct, infrared (IR) wireless communication, satellite communication, broadcast radio communication, Microwave radio communication, Bluetooth, Bluetooth Low Energy (BLE), Zigbee, near field communication (NFC), and radio frequency (RF) communication, USB, Firewire, and Ethernet.

The storage unit 113c may include a random access memory (RAM), a read-only memory (ROM), a hard disk, a flash drive, a database connected to the Internet, cloud-based storage, Internet-based storage, or any other type of storage unit.

The storage unit 113c may store data from the at least one sensor 111, such as the weight of the living being, the temperature level of the living being, the movement of the living being, the heartbeat of the living being, and/or the breathing of the living being. Additionally, the storage unit 113c may store data from the pulse oximeter 112, such as the level of oxygen saturation in the blood of the living being. As such, the pulse oximeter 112 may be connected to the pad 110 to store data on the storage unit 113c of the pad 110.

The at least one sensor 111 may be electrically connected to the control unit 113. Alternatively, the at least one sensor 111 may wirelessly communicate to the control unit 113. The pulse oximeter 112 may be electrically connected to the control unit 113. Alternatively, the pulse oximeter 112 may wirelessly communicate to the control unit 113.

The power source 114 may include a battery, such as lithium-ion, nickel cadmium, nickel metal hydride, alkaline, etc., but is not limited thereto.

The power source 114 may be disposed within at least a portion of the pad 110. The power source 114 may provide power to the at least one sensor 111, the pulse oximeter 112, and the control unit 113, but is not limited thereto.

The small fob 120 may include a body 121, a control unit 122, and a power source 123, but is not limited thereto.

Referring to FIG. 1, the small fob 120 is illustrated to be a necklace. However, the small fob 120 may be a bracelet, an armband, a legband, a headband, and a collar, but is not limited thereto. Alternatively, the small fob 120 may be an accessory removably connected to clothes, shoes, bags, etc., but is not limited thereto.

The control unit 122 may include a processing unit 122a and a communication unit 122b, but is not limited thereto.

The control unit 122 may be disposed within at least a portion of the body 121.

The processing unit 122a (or central processing unit, CPU) may include electronic circuitry to carry out instructions of a computer program by performing basic arithmetic, logical, control and input/output (I/O) operations specified by the instructions. The processing unit 122a may include an arithmetic logic unit (ALU) that performs arithmetic and logic operations, processor registers that supply operands to the ALU and store the results of ALU operations, and a control unit that fetches instructions from memory and "executes" them by directing the coordinated operations of the ALU, registers and other components. The processing unit 122a may also include a microprocessor and a microcontroller.

The communication unit 122b may include a device capable of wireless or wired communication between other wireless or wired devices via at least one of Wi-Fi, Wi-Fi Direct, infrared (IR) wireless communication, satellite communication, broadcast radio communication, Microwave radio communication, Bluetooth, Bluetooth Low Energy (BLE), Zigbee, near field communication (NFC), and radio frequency (RF) communication, USB, Firewire, and Ethernet.

The body 121 may be worn on at least a portion of a body of the living being. The processing unit 113a of the pad 110 may extract the data related to the living being from the storage unit 113c of the pad 110. Moreover, the processing unit 113a of the pad 110 may send a command to the communication unit 113b to send the data related to the living being to the communication unit 122b of the small fob 120. Alternatively, the processing unit 122a may send a command to the communication unit 122b to retrieve the data related to the living being from the control unit 113 of the pad 110, such that the processing unit 113a extracts the data related to the living being from the storage unit 113c and returns the data related to the living being to the processing unit 122a.

The power source 123 may be disposed within at least a portion of the body 121. The power source 123 may include a battery, such as lithium-ion, nickel cadmium, nickel metal hydride, alkaline, etc., but is not limited thereto.

The power source 123 may be disposed within at least a portion of the small fob 120. The power source 123 may provide power to the control unit 122, but is not limited thereto.

The at least one master fob 130 may include a body 131, a light 132, a beeper 133, a button 134, a control unit 135, a haptic unit 136, and a power source 137, but is not limited thereto.

The at least one master fob 130 may be a keychain, a necklace, a bracelet, an armband, a legband, and a headband, but is not limited thereto.

The control unit 135 may include a processing unit 135a, a communication unit 135b, and a storage unit 135c, but is not limited thereto.

The control unit 135 may be disposed within at least a portion of the body 131.

The processing unit 135a (or central processing unit, CPU) may include electronic circuitry to carry out instructions of a computer program by performing basic arithmetic, logical, control and input/output (I/O) operations specified by the instructions. The processing unit 135a may include an arithmetic logic unit (ALU) that performs arithmetic and logic operations, processor registers that supply operands to the ALU and store the results of ALU operations, and a control unit that fetches instructions from memory and "executes" them by directing the coordinated operations of the ALU, registers and other components. The processing unit 135a may also include a microprocessor and a microcontroller.

The communication unit 135b may include a device capable of wireless or wired communication between other wireless or wired devices via at least one of Wi-Fi, Wi-Fi Direct, infrared (IR) wireless communication, satellite communication, broadcast radio communication, Microwave radio communication, Bluetooth, Bluetooth Low Energy (BLE), Zigbee, near field communication (NFC), and radio frequency (RF) communication, USB, Firewire, and Ethernet.

The storage unit 135c may include a random access memory (RAM), a read-only memory (ROM), a hard disk, a flash drive, a database connected to the Internet, cloud-based storage, Internet-based storage, or any other type of storage unit.

The processing unit 122a of the small fob 120 may send a command to the communication unit 122b to send the data related to the living being to the communication unit 135b of the at least one master fob 130. Alternatively, the processing unit 113a of the pad 110 may send a command to the communication unit 113b to send the data related to the living being to the communication unit 135b of the at least one master fob 130. The communication unit 135b may send the data related to the living being to the processing unit 135a. The processing unit 135a may interpret existence of the data related to the living being to trigger an alert based on a plurality of predetermined conditions. In other words, the at least one master fob 130 may activate in response to the living being being disposed on the pad 110.

Furthermore, the processing unit 135a may send a storage command to the communication unit 135b, such that the data related to the living being is stored in the storage unit 135c. The processing unit 135a may request updated information from the processing unit 122a of the small fob 120 to keep the data related to the living being stored in the storage unit 135c synchronized. Alternatively, the processing unit 135a may request updated information from the processing unit 113a of the pad 110 to keep the data related to the living being stored in the storage unit 135c synchronized.

More specifically, the light 132 may be disposed on at least a portion of the body 131. Alternatively, the light 132 may be disposed within an indentation 131a on an end of the body 131. The light 132 may illuminate in response to an illumination command from the processing unit 135a based on the existence of the data related to the living being and a user's distance from the small fob 120. The light 132 may illuminate a predetermined color, such as red. The processing unit 135a may compare the user's distance to a predetermined distance from the small fob 120. Subsequently, the processing unit 135a may send the illumination command in response to the comparison, such that the user's distance at least equals the predetermined distance. For example, the processing unit 135 may send the illumination command in response to the user exceeding at least five feet from the small fob 120. The light 132 may illuminate a steady light and/or a flashing light.

Furthermore, the light 132 may vary in luminosity based on the data related to the living being. For example, the light 132 may be brighter in response to a first predetermined temperature or a second predetermined temperature that is dangerous for the living being to remain in the vehicle. As such, the data related to the living being may indicate the temperature level of the living being is above the first predetermined temperature (i.e. too hot) or below the second predetermined temperature (i.e. too cold), such that the living being may be at a substantial risk of death if the living being remains in the vehicle. Alternatively, the light 132 may be dimmer in response to the temperature level of the living being. Also, the light 132 may vary in luminosity in response to a drop in the level of oxygen saturation in the blood of the living being.

Additionally, the beeper 133 may be disposed on at least a portion of the body 131. Alternatively, the beeper 133 may be disposed within the indentation 131a on an end of the body 131, such as near the light 132. The beeper 133 may emit a sound in response to an auditory command from the processing unit 135a based on the existence of the data related to the living being and the user's distance from the small fob 120. The processing unit 135a may compare the user's distance to the predetermined distance from the small fob 120. Subsequently, the processing unit 135a may send the auditory command in response to the comparison, such that the user's distance at least equals the predetermined distance. For example, the processing unit 135 may send the auditory command in response to the user exceeding at least five feet from the small fob 120.

Furthermore, the beeper 133 may vary in volume based on the data related to the living being. For example, the beeper 133 may be louder in response to the first predetermined temperature or the second predetermined temperature that is dangerous for the living being to remain in the vehicle. As such, the data related to the living being may indicate the temperature level of the living being is above the first predetermined temperature or below the second predetermined temperature, such that the living being may be at a substantial risk of death if the living being remains in the vehicle. Alternatively, the beeper 133 may be low in volume in response to the temperature level of the living being. Also, the beeper 133 may vary in volume in response to a drop in the level of oxygen saturation in the blood of the living being.

Additionally, the haptic unit 136 may be disposed within at least a portion of the body 131. The haptic unit 136 may vibrate in response to a vibration command from the processing unit 135a based on the existence of the data related to the living being and the user's distance from the small fob 120. The processing unit 135a may compare the user's distance to the predetermined distance from the small fob 120. Subsequently, the processing unit 135a may send the vibration command in response to the comparison, such that the user's distance at least equals the predetermined distance. For example, the processing unit 135 may send the vibration command in response to the user exceeding at least five feet from the small fob 120.

Furthermore, the haptic unit 136 may vary in intensity based on the data related to the living being. For example, the haptic unit 136 may vibrate rapidly in response to the first predetermined temperature or the second predetermined temperature that is dangerous for the living being to remain in the vehicle. As such, the data related to the living being may indicate the temperature level of the living being is above the first predetermined temperature or below the second predetermined temperature, such that the living being may be at a substantial risk of death if the living being remains in the vehicle. Alternatively, the haptic unit 136 may vibrate slowly in response to the temperature level of the living being. Also, the haptic unit 136 may vary in intensity in response to a drop in the level of oxygen saturation in the blood of the living being.

Also, the light 132, the beeper 133, and the haptic unit 136 may activate in response to the movement of the living being, the heartbeat of the living being, and/or the breathing of the living being exceeding a predetermined threshold. Additionally, the light 132, the beeper 133, and the haptic unit 136 may collectively be an alert unit and/or separate individual components.

In other words, the user may receive at least one of a visual stimulation, an auditory stimulation, and a physical stimulation in response to the user being at least the predetermined distance away from the living being while the living being remains in the vehicle, and the existence of the data related to the living being.

The light 132 may illuminate until the user performs at least one of adjusting a vehicle temperature, removing a buckle from the child seat, and removing the living being from the vehicle. The beeper 133 may emit a sound until the user performs at least one of adjusting the vehicle temperature, removing the buckle from the child seat, and removing the living being from the vehicle. The haptic unit 136 may vibrate until the user performs at least one of adjusting the vehicle temperature, removing the buckle from the child seat, and removing the living being from the vehicle.

The button 134 may be disposed on at least a portion of the body 131. The button 134 may be depressed to terminate the alert. As such, the light 132, the beeper 133, and the haptic unit 136 may stop activating in response to the user depressing the button 134.

The power source 137 may be disposed within at least a portion of the body 131. The power source 137 may include a battery, such as lithium-ion, nickel cadmium, nickel metal hydride, alkaline, etc., but is not limited thereto.

The power source 137 may be disposed within at least a portion of the small fob 120. The power source 137 may provide power to the light 132, the beeper 133, the button 134, the control unit 135, and the haptic unit 136, but is not limited thereto.

The computing device 140 may include an input unit 141, a display unit 142, a processing unit 143, a communication unit 144, and a storage unit 145, but is not limited thereto.

The input unit 141 may include a keyboard, a touchpad, a mouse, a trackball, a stylus, a voice recognition unit, a visual data reader, a camera, a wireless device reader, and a holographic input unit.

The display unit 142 may include a plasma screen, an LCD screen, a light emitting diode (LED) screen, an organic LED (OLED) screen, a computer monitor, a hologram output unit, a sound outputting unit, or any other type of device that visually or aurally displays data.

Also, the display unit 142 may be combined with the input unit 141 to be a touch-screen.

The processing unit 143 (or central processing unit, CPU) may include electronic circuitry to carry out instructions of a computer program by performing basic arithmetic, logical, control and input/output (I/O) operations specified by the instructions. The processing unit 143 may include an arithmetic logic unit (ALU) that performs arithmetic and logic operations, processor registers that supply operands to the ALU and store the results of ALU operations, and a control unit that fetches instructions from memory and "executes" them by directing the coordinated operations of the ALU, registers and other components. The processing unit 143 may also include a microprocessor and a microcontroller.

The communication unit 144 may include a device capable of wireless or wired communication between other wireless or wired devices via at least one of Wi-Fi, Wi-Fi Direct, infrared (IR) wireless communication, satellite communication, broadcast radio communication, Microwave radio communication, Bluetooth, Bluetooth Low Energy (BLE), Zigbee, near field communication (NFC), and radio frequency (RF) communication, USB, Firewire, and Ethernet.

The storage unit 145 may include a random access memory (RAM), a read-only memory (ROM), a hard disk, a flash drive, a database connected to the Internet, cloud-based storage, Internet-based storage, or any other type of storage unit.

For ease of description, the computing device 140 will be hereinafter interpreted to be a smart phone with a touch-screen.

The computing device 140 may access the Internet via the communication unit 144 to allow the user to access a website, and/or may allow a program and/or an application to be executed using the processing unit 143. For ease of description, the program and/or the application will be hereinafter referred to as an app. The app may be downloaded from the Internet to be stored on the storage unit 145. Moreover, the app may be designed to alert the user in response to the user being the predetermined distance away from the small fob 120, and the existence of the data related to the living being. Alternatively, the app may receive the data related to the living being from at least one of the control unit 113 of the pad 110, the control unit 122 of the small fob 120, and the control unit 135 of the at least one master fob 130. As such, the app may monitor at least one of the weight of the living being, the temperature level of the living being, and the level of oxygen saturation in the blood of the living being.

As such, the app may cause the processing unit 143 to send a command to the display unit 141 to illuminate and/or flash the display unit 141 in response to the user being the predetermined distance away from the small fob 120, and the existence of the data related to the living being. Alternatively, the display unit 141 may display a warning message in response to the command from the processing unit 143 based on the data related to the living being and the user's distance from the small fob 120.

The user may add another at least one master fob 130 to receive data from the small fob 120 and to interact with the pad 110 and/or the computing device 140. Specifically, the app may randomly generate a code that is stored on the storage unit 113*c* of the pad 110 that links to the another at least one master fob 130, such that the another at least one master fob 130 may receive the data related to the living being sent from the control unit 113 of the pad 110. Moreover, the code may be stored on the storage unit 145 of the computing device 140 to create the another at least one master fob 130. As such, the user may provide the another at least one master fob 130 to trusted friends and/or family members.

Furthermore, the app may cause the processing unit 143 to send an assist signal from the communication unit 144 to a third party in response to the user's failure to return to the vehicle within a predetermined amount of time and/or the user's failure to assist the living being, such as adjusting a temperature level within the vehicle and/or removing the living being from the vehicle. The third party may include an emergency response team (e.g., police, emergency medical technicians), a family member, and/or a trusted friend. Any contact information for the third party may be stored in the storage unit 145.

Therefore, the alert system 100 may provide a powerful reminder to the user in situations where the user forgets that the living being has been left behind in the vehicle. The alert system 100 may include redundancy as a backup to improper working components. For example, the pad 110 may communicate directly with the at least one master fob 130 and/or the computing device 140. As such, the alert system 100 may prevent many people and/or animals from accidental death.

Therefore, the alert system 100 may prevent abandonment of the living being in the vehicle. The alert system 100 may include the pad 110 removably disposed on at least a portion of the interior of the vehicle to monitor and may store the data related to the living being in response to the living being being disposed on the pad 110, and the at least one master fob 130 may receive the data related to the living being from the pad 110, and may generate an alert in response to the at least one master fob 130 being moved the predetermined distance away from the pad 110, and based on at least a portion of the received data indicating that that the living being may be disposed on the pad 110.

The alert system 100 may further include the pulse oximeter 112 to detect the level of oxygen saturation in blood of the living being.

The pulse oximeter 112 may monitor the level of oxygen saturation in the blood of the living being in response to the living being disposed on the pad 110.

The pulse oximeter 112 may monitor the level of oxygen saturation in the blood of the living being in response to the pulse oximeter 112 being connected to the living being.

The pulse oximeter 112 may be disposed within at least a portion of the pad 110.

The pulse oximeter 112 may be a wearable device.

The alert system 100 may further include the small fob 120 removably connected to the living being to receive the data related to the living being from the pad 110.

The small fob 120 may transmit the data related to the living being to the at least one master fob 130.

The alert system 100 may further include the computing device 140 including the app executed thereon, the app monitoring the data related to the living being received from the pad 110.

The app may alert the third party in response to at least one of the user's failure to return to the vehicle within the predetermined amount of time and the user's failure to assist the living being.

Assisting the living being may include removing the living being from the vehicle.

The app may randomly generate a code to be stored on the pad 110 and the another at least one master fob 130, such that the another at least one master fob 130 may receive the data related to the living being from the pad 110.

The data related to the living being may be at least one of the weight of the living being, the temperature level of the living being, the movement of the living being, the heartbeat of the living being, and the breathing of the living being.

The pad 110 may monitor data related to the living being in the vehicle, the pad 110 including the at least one sensor 111 disposed within at least a portion of the pad 110 to detect information relating to the living being, and the communication unit 113*b* may send the information related to the living being to an external device such that the external device may be alerted that the living being is disposed on the pad 110.

The pad 110 may further include the pulse oximeter 112 disposed within at least a portion of the pad 110 to monitor the level of oxygen saturation in the blood of the living being.

The information relating to the living being may be at least one of the weight of the living being and the temperature level of the living being.

The at least one master fob 130 may include the body 131, the indentation 131*a* may be disposed on at least a portion of the end of the body 131 to store the alert unit therein, the communication unit 135*b* may be disposed within at least a portion of the body 131 to receive the data related to the living being from an external device, the processing unit 135*a* may be disposed within at least a portion of the body to generate the alert in response to the body 131 being moved the predetermined distance away from the vehicle, and based on at least a portion of the received data indicating that that the living being is disposed in the vehicle, and the alert unit may be disposed within at least a portion of the indentation 131*a* to generate at least one of an illumination, a sound, and a vibration in response to the alert and the at least a portion of the received data indicating that that the living being may be disposed in the vehicle.

The alert unit may include at least one of the light 132, the beeper 133, and the haptic unit 136, but is not limited thereto.

The at least one master fob 130 may further include the button 134 disposed on at least a portion of the body 131 to terminate the alert signal.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

The invention claimed is:

1. An alert system to prevent abandonment of a living being in on a seat in a vehicle, the alert system comprising:
   a pad including a randomly generated code stored thereon, the pad removably disposed on at least a portion of an interior of the vehicle to monitor and store data related to the living being in response to the living being being disposed on the pad, such that the pad covers at least a portion of a back portion of the seat and a base portion of the seat, such that the pad receives data related to the living being corresponding to the back portion of the seat and the base portion of the seat, such that the pad is flexible to assume a shape of any surface upon which it is placed, such that the pad measures a level of oxygen saturation in blood of the living being and detects fluctuations in the level of oxygen saturation as a result of the living being breathing in the vehicle while the vehicle is turned off; and at least one master fob including the randomly generated code store thereon, the at least one master fob to receive the data related to the living being from the pad in response to having the randomly generated code thereon and to generate an alert in response to the master fob being moved a predetermined distance away from the pad and based on at least a portion of the received data indicating that that the living being is disposed on the pad.

2. The alert system of claim 1, further comprising:

a pulse oximeter to detect the level of oxygen saturation in blood of the living being.

3. The alert system of claim 2, wherein the pulse oximeter monitors the level of oxygen saturation in the blood of the living being in response to the living being being disposed on the pad.

4. The alert system of claim 2, wherein the pulse oximeter monitors the level of oxygen saturation in the blood of the living being in response to the pulse oximeter being connected to the living being.

5. The alert system of claim 2, wherein the pulse oximeter is disposed within at least a portion of the pad.

6. The alert system of claim 2, wherein the pulse oximeter is a wearable device.

7. The alert system of claim 1, further comprising:

a small fob removably connected to the living being to receive the data related to the living being from the pad.

8. The alert system of claim 7, wherein the small fob transmits the data related to the living being to the at least one master fob.

9. The alert system of claim 1, further comprising:

a computing device including an app executed thereon, the app monitoring the data related to the living being received from the pad.

10. The alert system of claim 9, wherein the app alerts a third party in response to at least one of the user's failure to return to the vehicle within a predetermined amount of time and the user's failure to assist the living being.

11. The alert system of claim 10, wherein assisting the living being is removing the living being from the vehicle.

12. The alert system of claim 1, wherein the data related to the living being is at least one of a weight of the living being, a temperature level of the living being, a movement of the living being, a heartbeat of the living being, and breathing of the living being.

13. A pad having a randomly generated code to monitor data related to the living being on a seat in a vehicle, the pad comprising:

at least one sensor disposed within at least a portion of the pad to detect information relating to the living being, such that the at least one sensor within the pad covers at least a portion of a back portion of the seat and a base portion of the seat, such that the at least one sensor receives data related to the living being corresponding to the back portion of the seat and the base portion of the seat, such that the at least one sensor is flexible to assume a shape of any surface upon which it is placed, such that the pad measures a level of oxygen saturation in blood of the living being and detects fluctuations in the level of oxygen saturation as a result of the living being breathing in the vehicle while the vehicle is turned off; and a communication unit to send the information related to the living being to an external device having the randomly generated code from the pad, such that the external device is alerted that the living being is disposed on the pad.

14. The pad of claim 13, further comprising:

a pulse oximeter disposed within at least a portion of the pad to monitor a level of oxygen saturation in blood of the living being.

15. The pad of claim 13, wherein the information relating to the living being is at least one of a weight of the living being, a temperature level of the living being, a movement of the living being, a heartbeat of the living being, and breathing of the living being.

* * * * *